United States Patent [19]

Foster et al.

[11] Patent Number: 5,384,305

[45] Date of Patent: Jan. 24, 1995

[54] HERBICIDAL CARBOXAMIDE COMPOUNDS

[75] Inventors: Christopher J. Foster, Faversham; Terence Gilkerson, Canterbury; Richard Stocker, Rochester; Ian J. Gilmore, Sittingbourne, all of England

[73] Assignee: Shell Research Limited, United Kingdom

[21] Appl. No.: 787,647

[22] Filed: Nov. 4, 1991

[30] Foreign Application Priority Data

Nov. 28, 1990 [GB] United Kingdom ............... 9025828

[51] Int. Cl.⁶ .................... C07D 213/56; A01N 43/40
[52] U.S. Cl. ...................... 504/130; 504/136; 544/124; 544/360; 546/193; 546/291
[58] Field of Search ............... 546/298, 291, 193; 504/300, 130, 136; 544/124, 360

[56] References Cited

U.S. PATENT DOCUMENTS

| | | | |
|---|---|---|---|
| 4,251,263 | 2/1981 | Gutman | 546/291 |
| 4,270,946 | 6/1981 | Gutman | 546/291 |
| 4,327,218 | 4/1982 | Gutman | 546/291 |
| 4,329,167 | 5/1982 | Rempfler et al. | 71/94 |
| 4,384,882 | 5/1983 | Rempfler et al. | 71/94 |
| 4,425,157 | 1/1984 | Rempfler et al. | 71/94 |
| 4,433,998 | 2/1984 | Rempfler et al. | 71/94 |
| 4,443,247 | 4/1984 | Rempfler et al. | 71/94 |
| 4,558,134 | 12/1985 | Tong | 546/298 |
| 4,618,366 | 10/1986 | Cramp et al. | 71/94 |

FOREIGN PATENT DOCUMENTS

| | | | |
|---|---|---|---|
| 0000176 | 1/1979 | European Pat. Off. | 71/94 |
| 0292032 | 11/1988 | European Pat. Off. | 546/291 |
| 1371939 | 10/1974 | United Kingdom | 546/291 |

*Primary Examiner*—C. Warren Ivy
*Assistant Examiner*—Zinna N. Davis

[57] ABSTRACT

Compounds of the formula

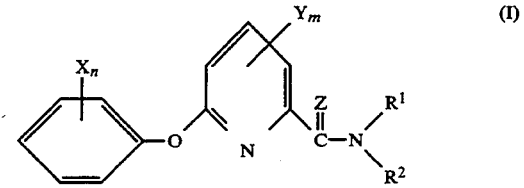

wherein
n is 1 to 5 and the/each X is hydrogen, halogen, cyano, nitro, optionally substituted alkyl or alkoxy alkenyloxy, alkynyloxy, haloalkylthio, alkenylthio or alkynylthio;
m is 0 or 1 to 3 and the/each Y is halogen, alkyl or haloalkyl;
Z is oxygen or sulphur;
and
$R^1$ and $R^2$ each, independently, is hydrogen, alkyl optionally substituted by halogen, hydroxy, cyano, alkoxy, alkylthio, alkoxycarbonyl, or mono- or di-alkylamino, alkenyl, alkynyl, hydroxy, alkoxy, alkenyloxy, alkynyloxy, alkoxycarbonyl, amino, mono- or di-alkylamino, alkoxycarbonylamino, arylamino, dialkylcarbamoyl, cycloalkyl, or optionally substituted cycloalkylalkyl;
or
$R^1$ and $R^2$ together form an alkylene chain optionally interrupted by oxygen, sulphur or —NR—, R being hydrogen or alkyl;
are herbicides.

9 Claims, No Drawings

HERBICIDAL CARBOXAMIDE COMPOUNDS

The present invention relates to herbicidal carboxamide derivatives, their preparation, herbicidal compositions containing such derivatives and their use in combating undesired plant growth.

The herbicidal activity of 2-phenoxy-3-pyridine carboxamide compounds is well known. In 1981 and 1982 three U.S. Pat. Nos. were published, Nos. 4,251,263, 4,270,946 and 4,327,218, directed to A. D. Gutman's work on 2-phenoxynicotinamide herbicides. His later review article, Chapter 5 of "Synthesis and Chemistry of Agrochemicals" (1987) published by the American Chemical Society, shows that his investigations started with 2-phenoxynicotinic acids (which were found to be inactive) progressed to N-alkyl amide derivatives (found to have weak herbicidal activity), and then concentrated on N-phenyl and N-benzyl amides as the most active of the compound type. Indeed, Diflufenican[N-(2,4-difluorophenyl)-2-(3-trifluoromethylphenoxy)-3-pyridine carboxamide] was subsequently developed, by a different research group, as a commercial herbicide for use against broad-leaved weeds in winter cereals, such as winter wheat and barley.

U.S. Pat. No. 4,251,263 is concerned with the N-alkyl amides of Gutman, and related N-alkenyl and N-alkynyl amides. The compound documented as being the most active of the aliphatic amides prepared and tested is N-(1,1-dimethylprop-2-ynyl)-2-(3-trifluoromethylphenoxy)-3-pyridine carboxamide, which gives 85% control preemergence and only 57% control postemergence on specified narrow- and broad-leaved species.

Suprisingly, it has now been found that 2-phenoxy-6-pyridine carboxamide compounds with aliphatic (both straight chain and alicyclic) and other substitution of the amide nitrogen atom have unexpectedly high levels of herbicidal activity against representative narrow- and broad-leaved test species in pre- and/or post-emergence application; certain examples exhibiting 90 to 100% effectiveness against test species both pre- and post-emergence.

The present invention accordingly provides a compound of the general formula I

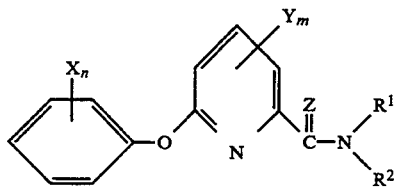

wherein n is an integer from 1 to 5 and the or each X independently represents a hydrogen or halogen atom, an alkyl or alkoxy group optionally substituted by one or more of the same or different substituents selected from halogen atoms and cyano, hydroxy and alkoxy groups, or a cyano, nitro, alkenyloxy, alkynyloxy, alkylthio, haloalkylthio, alkenylthio or alkynylthio group;

m is 0 or an integer from 1 to 3 and the or each Y independently represents a halogen atom or an alkyl or haloalkyl group;

Z represents an oxygen atom or a sulphur atom; and $R^1$ and $R^2$ each, independently, represents a hydrogen atom, an alkyl group optionally substituted by one or more of the same or different substituents selected from halogen atoms or hydroxy, cyano, alkoxy, alkylthio, alkoxycarbonyl, or mono- or di-alkylamino groups, an alkenyl, alkynyl, cycloalkyl, or optionally substituted cycloalkylalkyl group, or a hydroxy, alkoxy, alkenyloxy, alkynyloxy, alkoxycarbonyl, amino, mono- or di-alkylamino, alkoxycarbonylamino group, an arylamino group optionally substituted by a halogen atom, or a dialkylcarbamoyl group;

or $R^1$ and $R^2$ together represent an alkylene chain which is optionally interrupted by an oxygen or sulphur atom or by a group —NR— in which R represents a hydrogen atom or an alkyl group.

When any of the substituents X, Y, $R^1$ and $R^2$ represents or contains an alkyl, alkenyl or alkynyl substituent group, this may be linear or branched and suitably has up to 12, preferably up to 8 and especially up to 5, carbon atoms. Thus, for example, an alkyl group $R^2$ may be butyl, e.g. i-butyl, n-butyl, sec-butyl or tert-butyl. Where a cycloalkyl substituent group is present, this suitably has from 3 to 8, preferably 3 to 6, carbon atom ring atoms. An aryl group is suitably phenyl. An alkylene chain suitably has 3 to 6, preferably 4 or 5, chain members. A halogen atom suitably denotes a fluorine, chlorine, bromine or iodine atom; preferred haloalkyl groups are trifluoromethyl, trifluoroethyl and fluoroethyl.

The substituent(s) $X_n$ may be at any free position or combination of positions on the phenoxy ring.

One phenoxy substituent X is desirably located at the 3- (or meta-) position and is preferably a hydrogen, fluorine, chlorine or bromine atom or a nitro, ethyl, methoxy or, especially, a trifluoromethyl group. When additional substituents X are present, they are suitably located at the 4- and/or 5- position and may be the same as, or, preferably, different to the meta-substituent. Such additional substituent(s), X, are preferably selected from chlorine and, especially, fluorine atoms.

Substituent(s) $X_n$ may, of course, be at other positions, and may be, for example, 2,3- or 2,5-dimethyl.

Preferably only one or two substituents X are present and, most preferably one of or the X represents a 3-trifluoromethyl substituent.

Preferably m is 0.

Preferably Z represents an oxygen atom.

The radicals $R^1$ and $R^2$ when individually present may be the same or different. Preferably $R^1$ represents a hydrogen atom or a $C_{1-4}$ alkyl or $C_{2-4}$ alkenyl, suitably allyl, group, most preferably hydrogen or $C_{1-4}$ alkyl, while $R^2$ represents an unsubstituted $C_{1-8}$ alkyl group, especially $C_{1-6}$ alkyl, a $C_{1-4}$ alkyl group substituted by fluorine, hydroxy, cyano, $C_{1-2}$ alkoxy, ($C_{1-2}$ alkoxy)carbonyl, or mono- or di-($C_{1-2}$ alkyl)amino, for example fluoroethyl, trifluoroethyl, cyanopropyl, hydroxyethyl, methoxyethyl, ethoxycarbonylmethyl, or dimethylaminoethyl, a $C_{3-8}$ cycloalkyl group, especially cyclopropyl, cyclobutyl, cyclopentyl or cyclohexyl, a $C_{2-4}$ alkenyl group, for example allyl or methylallyl, a $C_{2-4}$ alkynyl group, for example propynyl, a $C_{1-4}$ alkoxy group, for example ethoxy, a ($C_{1-4}$ alkyl)amino group, for example methylamino, a $C_{2-4}$ alkenyloxy group, for example propenyloxy, a ($C_{1-2}$ alkoxy)carbonyl group, for example ethoxycarbonyl, a ($C_{1-2}$ alkoxy)carbonylamino group, for example ethoxycarbonylamino, a di($C_{1-2}$ alkyl)carbamoyl group, for example dimethylcarbamoyl, an arylamino group, for example phenylamino or p-chlorophenylamino, or a halo-substituted (C$_{3-6}$ cycloalkyl)C$_{1-4}$ alkyl group, for example chloro-substituted cyclopropylmethyl.

It is especially preferred that either R$^1$ represents a hydrogen atom while R$^2$ represents an unsubstituted C$_{1-5}$ alkyl group, a C$_{1-2}$ alkyl group substituted by fluorine or methoxy, a C$_{3-6}$ cycloalkyl group, a C$_3$ alkenyl group, a C$_3$ alkynyl group, a C$_{1-2}$ alkoxy group, a C$_3$ alkenyloxy group or a chloro-substituted cyclopropylmethyl group, or R$^1$ represents a C$_{1-3}$ alkyl group while R$^2$ represents the same C$_{1-3}$ alkyl group or a chloro-substituted cyclopropylmethyl group.

Particularly preferred are compounds in which R$^1$ represents a hydrogen atom and R$^2$ represents an ethyl, propyl, cyclopropyl or cyclobutyl group.

When R$^1$ and R$^2$ together represent an alkylene chain, suitably the chain consists of 4 or 5 chain atoms, and is for example a group —(CH$_2$)$_4$—, —(CH$_2$)$_2$O(CH$_2$)$_2$— or —(CH$_2$)$_2$NR(CH$_2$)$_2$— in which R is a C$_{1-2}$ alkyl group, suitably methyl. Preferably R$^1$ and R$^2$ is a —(CH$_2$)$_4$— group.

The compounds of general formula I may be prepared either by reaction of an appropriate phenoxypicolinic acid derivative with an appropriate amine (method A) or by reaction of an appropriate 2-halo-6-pyridine carboxamide derivative with an appropriate alkali metal phenolate (method B). Such methods constitute further aspects of the present invention.

In accordance with method A, a compound of the general formula I in which Z is oxygen, is prepared by reacting a compound of the general formula II

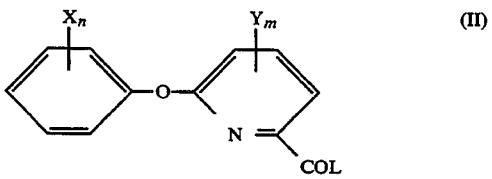

(II)

in which X$_n$ and Y$_m$ are as hereinbefore defined and L represents a leaving group, with an amine of the general formula NHR$^1$R$^2$ in which R$^1$ and R$^2$ are as defined above.

A leaving group is any group that will, under the reaction conditions, cleave from the starting material thus promoting reaction at a specific site.

The leaving group L may suitably be a halogen atom, for example a bromine or, especially, a chlorine atom or an alkoxy group, suitably C$_{1-4}$ alkoxy, especially methoxy.

The process variant A is suitably carried out in the presence of an inert organic solvent, for example dimethylformamide or an aromatic hydrocarbon, for example benzene or toluene, or a halogenated hydrocarbon, for example dichloromethane or an ether, for example diethyl ether, or an ester, for example ethyl acetate; suitably at a temperature in the range of from 0° to 100° C.

Suitably, the reaction is carried out using substantially equimolar amounts of the reactants. However, it can be expedient to use one reactant in excess, conveniently the amine, for example such that the molar ratio of phenoxypicolinic acid derivative to amine is in the range 1:1 to 1.1.

When L represents a halogen atom the reaction is suitably carried out at a temperature in the range 0° to 50° C., preferably at ambient temperature, and suitably in the presence of a base, for example potassium carbonate or, preferably, an amine base, such as triethylamine or excess amine starting material.

When L represents an alkoxy group the reaction is suitably carried out at a temperature in the range 0° to 100° C., preferably at room temperature (or 20° C.) and in the absence of an added base.

In accordance with method B, a compound of the general formula I in which Z is oxygen, is prepared by reacting a compound of the general formula III

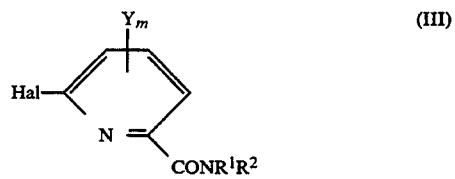

(III)

in which Y$_m$, R$^1$ and R$^2$ are as defined above and Hal represents a halogen atom with a compound of the general formula IV

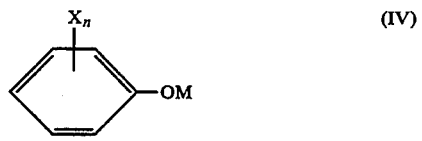

(IV)

in which X$_n$ is as defined above and M represents an alkali metal atom.

Suitably, Hal represents a bromine atom or, especially, a chlorine atom. Suitably, R represents a potassium atom or, especially, a sodium atom.

The reaction B may be carried out by preparation of the alkali metal phenolate from the phenol using an alkali metal alkoxide, such as sodium methoxide, followed by treatment of the phenolate with a substantially equimolar amount of reactant III, suitably at an elevated temperature, for example under reflux, with a copper catalyst, such as cuprous chloride, in pyridine in the presence of an aromatic hydrocarbon, such as xylene, as is described in U.K. Patent Specification No. 2 050 168A.

Alternatively the process variant B could be carried out in the presence of an alkali metal hydride, for example sodium hydride, in a dry solvent, such as dimethylformamide, suitably at an elevated temperature, for example at a temperature in the range of from 50° C. to 125° C., or in the presence of an alkali metal carbonate, for example sodium or potassium carbonate, followed by treatment with cuprous oxide and/or copper powder in an organic solvent, such as dimethylformamide or quinoline, suitably at a temperature in the range of from 20° to 150° C. and conveniently at the reflux temperature of the reaction mixture.

Compounds of the general formula I wherein Z represents a sulphur atom are suitably prepared by reaction of a compound of the general formula I wherein Z represents an oxygen atom, with phosphorous pentasulphide under standard conditions, for example by heating, suitably under reflux, in the presence of an inert aromatic solvent, for example benzene, toluene, pyridine or quinoline.

The compounds of the present invention may be isolated and purified by conventional techniques, for example by solvent extraction, evaporation followed by recrystallisation or by chromatography on silica.

Compounds of formula II may be prepared from corresponding phenoxy-substituted picolinic acids by standard methods for the preparation or, for example, esters, using, for example, alcohols and acid catalysts or thionyl chloride, or of acid chlorides and acid bromides, using, for example, thionyl chloride or thionyl bromide. The acid compounds themselves can be prepared by standard methods from chloropicolinic acid or ester thereof. Chloropicolinic acid, or ester thereof, may be prepared by the methods described in J. Pharm. Belg. (1980), 35 1, 5–11.

Compounds of formula III may suitably be prepared by an analogous method to that of method A, by reacting a substituted amine of formula $NHR^1R^2$ with a 2-halo-6-pyridine carboxylic acid derivative of the general formula V

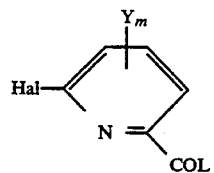
V in which $Y_m$, Hal and L are as defined above. Compounds of formula V may be prepared by conventional techniques from picolinic acid.

The substituted amines $NHR^1R^2$ and the phenolates of formula IV are either known or can be prepared by conventional techniques.

The compounds of the invention have been found to have a surprisingly high herbicidal activity with a wide spectrum of activity against grasses and, especially, broadleaved weeds, including *Alopecurus myosuroides* (blackgrass), *Avena fatua* (wild oat), *Steria faberii* (giant foxtail), *Setaria viridis* (green foxtail), *Ipomoea purpurea* (morning glory), *Galium aparine* (cleavers), *Solanum nigrum* (black nightshade), *Veronica persica* (speedwell) and *Stellaria media* (chickweed), when applied pre- and post-emergence. Examples have been found to show selectivity to small grain cereals, for example maize, wheat, barley and rice, and to broad-leaved crops, for example soya, sunflower and cotton, indicating that they may be useful in combating weeds growing in such crops.

The invention further provides a herbicidal composition comprising a compound of formula I as defined above in association with a carrier, and a method of making such a composition which comprises bringing a compound of formula I into association with a carrier.

The invention also provides the use of such a compound or composition according to the invention as a herbicide. Further in accordance with the invention there is provided a method of combating undesired plant growth at a locus by treating the locus with a compound or composition according to the invention. Application to the locus may be pre-emergence or post-emergence. The dosage of active ingredient used, may, for example, be in the range of from 0.01 to 10 kg/ha, suitably 0.05 to 4 kg/ha. The locus may, for example, be the soil or plants in a crop area, typical crops being cereals such as wheat and barley, and broad-leaved crops, such as soya, sunflower and cotton.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example compounds possessing insecticidal or fungicidal properties or other herbicides.

The following Examples illustrate the invention. Example 1 illustrates the preparation of an ester of general formula II and Examples 2 to 63 relate to the preparation of compounds of general formula I; Examples 2 to 61 by Method A, Example 62 by Method B, and Example 63 by conversion of a compound of general formula I in which Z is oxygen to one in which Z is sulphur. All structures were confirmed by mass spectroscopy and-/or 300'H nmr.

EXAMPLE 1

Preparation of methyl-6-(3-α,α,α-trifluoromethylphenoxy)picolinate

A solution of sodium methoxide (from 1.3 g sodium in 20 ml methanol) was added to a solution of 3-α,α,α-trifluoromethylphenol (8.9 g) in xylene (50 ml). The solvents were evaporated in vacuo to give the dry sodium phenolate. Pyridine (25 ml) and xylene (50 ml) were added, followed by cuprous chloride (1.5 g) and the mixture heated to reflux. A solution of methyl-6-chloropicolinate (8.5 g) in xylene (50 ml) was added dropwise. The mixture was refluxed for a further 14 hours. After cooling, the mixture was poured into water (500 ml) and acidified with dilute sulphuric acid. The xylene layer was separated and the aqueous layer further extracted with diethyl ether. The combined extracts were washed with brine, dried over anhydrous magnesium sulphate and evaporated. The residue was purified on a silica gel column using 5% (v/v) diethyl ether/dichloromethane as eluant to give the title compound (7.4 g) as a yellow solid of melting point 43°-44° C.

| Analysis (%): | | | | |
|---|---|---|---|---|
| $C_{14}H_{10}O_3NF_3$ | Calc.: | C 56.6 | H 3.4 | N 4.7 |
| | Found: | C 55.6 | H 3.4 | N 4.8 |
| m/e: | Theory: | 297 | | |
| | Found: | 297 | | |

EXAMPLE 2

N-n-propyl-2-(3-α,α,α-trifluoromethylphenoxy)-6-pyridine carboxamide (a) Preparation of 6-(3-α,α,α-trifluoromethylphenoxy) picolinic acid A solution of methyl-6-(3-α,α,α-trifluoromethylphenoxy)-picolinate (8 g) in 50% aqueous methanol (45 ml) containing sodium hydroxide (2.5 g) was refluxed for 3 hours. The methanol was evaporated, more water added to the residue and the aqueous solution extracted with diethyl ether. The aqueous phase was then acidified with dilute hydrochloric acid to precipitate 6-(3-α,α,α-trifluoromethylphenoxy)picolinic acid (7.1 g) as a white solid of melting point 92°-93° C.

| Analysis (%): | | | | |
|---|---|---|---|---|
| $C_{13}H_8NO_3F_3$ | Calc: | C 55.1 | H 2.8 | N 4.9 |
| | Found: | C 53.3 | H 3.0 | N 5.0 |
| m/e | Theory: | 283 | | |
| | Found: | 283 | | | b) Preparation of N-n-propyl-2-(3-α,α,α-trifluoromethylphenoxy)-6-pyridine carboxamide 6-(3-α,α,α-trifluoromethylphenoxy)picolinic acid (1.5 g) in thionyl chloride (20 ml) was refluxed for 1 hour. The excess thionyl chloride was evaporated in vacuo and dichloromethane (20 ml) added to the residual picolinoyl chloride. A solution of n-propylamine (0.6 g) and triethylamine (1.0 g) in dichloromethane (20 ml) was added dropwise at ambient temperature. After stirring for a further ½ hour, the reaction mixture was washed with water, dried over anhydrous magnesium sulphate and the dichloromethane evaporated off. The residue was purified on a silica gel column using 5% (v/v) diethyl ether/dichloromethane as eluant to give N-n-propyl-2-(3-α,α,α-trifluoromethylphenoxy-6-pyridine carboxamide (1.5 g) as an oil.

| Analysis (%): | | | | |
|---|---|---|---|---|
| $C_{16}H_{15}O_2N_2F_3$ | Calc.: | C 59.3 | H 4.6 | N 8.6 |
| | Found: | C 60.0 | H 5.0 | N 8.7 |
| m/e | Theory: | 324 | | |
| | Found: | 324 | | |

EXAMPLE 2A

Preparation of N-n-propyl-2-(3-α,α,α-trifluoromethylphenoxy)-6-pyridine carboxamide Methyl-6-(3-α,α,α-trifluoromethylphenoxy) picolinate (0.8 g) and n-propylamine (1.4 g, excess) were allowed to stand at room temperature for one hour. The excess n-propylamine was evaporated leaving the title compound (0.7 g) as a colourless oil.

| Analysis (%): | | | | |
|---|---|---|---|---|
| $C_{16}H_{15}O_2N_2F_3$: | Calc.: | C 59.2 | H 4.6 | N 8.6 |
| | Found: | C 58.6 | H 4.9 | N 8.8 |
| m/e | Theory: | 324 | | |
| | Found: | 324 | | |

EXAMPLES 3 TO 61

Further compounds of the general formula I were prepared by the procedure of Example 2 above, with the appropriate selection of starting materials. Details of the compounds of formula I prepared are given in Table 1 below, and of the starting acids are given in Table 2.

TABLE 1

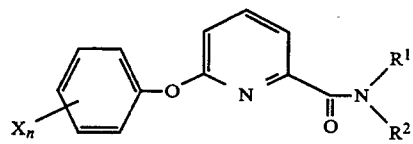

(I)

| Example No. | $X_n$ | $R^1$ | $R^2$ | C (Calc. Found) | H (Calc. Found) | N (Calc. Found) | Melting Point (°C.) | m/e (Theory Found) |
|---|---|---|---|---|---|---|---|---|
| 3 | 3-CF$_3$ | H | nC$_4$H$_9$ | 60.3 / 59.8 | 5.0 / 5.2 | 8.3 / 8.5 | oil | 338 / 338 |
| 4 | 3-CF$_3$ | H | sC$_4$H$_9$ | 60.3 / 60.1 | 5.0 / 5.4 | 8.3 / 8.5 | oil | 338 / 338 |
| 5 | 3-CF$_3$ | H | tC$_4$H$_9$ | 60.3 / 60.0 | 5.0 / 5.2 | 8.3 / 8.6 | oil | 338 / 338 |
| 6 | 3-Cl | H | nC$_4$H$_9$ | 63.1 / 62.6 | 5.6 / 5.9 | 9.2 / 9.1 | oil | 304 / 304 |
| 7 | 3-CF$_3$ | C$_2$H$_5$ | C$_2$H$_5$ | 60.4 / 59.7 | 5.0 / 5.3 | 8.3 / 8.3 | oil | 338 / 338 |
| 8 | 3-CF$_3$ | H | CH$_2$CH=CH$_2$ | 59.6 / 57.7 | 4.0 / 3.9 | 8.7 / 8.7 | 34–36 | 322 / 322 |
| 9 | 3-CF$_3$ | H | CH$_2$CH$_2$OCH$_3$ | 56.5 / 55.1 | 4.4 / 4.5 | 8.2 / 7.9 | oil | 340 / 340 |
| 10 | 3-CF$_3$ | —CH$_2$—CH$_2$—O—CH$_2$—CH$_2$— | | 58.0 / 57.3 | 4.3 / 4.5 | 8.0 / 7.8 | oil | 352 / 352 |
| 11 | 3-CF$_3$ | —CH$_2$—CH$_2$—CH$_2$—CH$_2$— | | 60.7 / 61.1 | 4.5 / 4.6 | 8.3 / 8.3 | 98–99 | 336 / 336 |
| 12 | 3-CF$_3$ | nC$_3$H$_7$ | nC$_3$H$_7$ | 62.3 / 62.3 | 5.7 / 6.1 | 7.7 / 7.7 | oil | 366 / 366 |
| 13 | 3-CF$_3$ | H | CH$_2$CH$_2$N(CH$_3$)$_2$ | 57.8 / 57.6 | 5.1 / 5.2 | 11.9 / 11.9 | 58–59 | 353 / 353 |
| 14 | 3,4-diCl | H | nC$_4$H$_9$ | 56.8 / 59.2 | 4.7 / 6.1 | 8.3 / 8.9 | oil | 338 / 338 |
| 15 | 3-CF$_3$,4-F | H | nC$_4$H$_9$ | 57.3 / 57.5 | 4.5 / 5.1 | 7.9 / 8.0 | oil | 356 / 356 |
| 16 | 3-Br | H | nC$_4$H$_9$ | 55.0 / 58.0 | 4.9 / 5.3 | 8.0 / 8.1 | oil | 349 / 349 |
| 17 | 3,5-diCl | H | nC$_4$H$_9$ | 56.8 / 53.0 | 4.7 / 5.2 | 8.3 / 7.6 | oil | 338 / 338 |
| 18 | 3-NO$_2$ | H | nC$_4$H$_9$ | 61.0 / 57.3 | 5.4 / 6.0 | 13.3 / 12.3 | oil | 315 / 315 |
| 19 | 3-CF$_3$ | H | iC$_3$H$_7$ | 59.3 / 58.9 | 4.6 / 4.9 | 8.6 / 8.4 | oil | 324 / 324 |
| 20 | 3-CF$_3$ | H | nC$_5$H$_{11}$ | 61.4 / 60.8 | 5.4 / 5.4 | 8.0 / 9.7 | oil | 352 / 352 |
| 21 | 3-CF$_3$ | H | nC$_6$H$_{13}$ | 62.3 / 62.1 | 5.7 / 5.7 | 7.6 / 7.5 | 44–45 | 366 / 366 |
| 22 | 3-CF$_3$ | H | C$_2$H$_5$ | 58.1 / 58.4 | 4.2 / 4.1 | 9.0 / 8.9 | 30 | 310 / 310 |
| 23 | 3-CF$_3$ | H | CH$_2$C≡CH | 60.0 / 59.8 | 3.4 / 3.7 | 8.7 / 8.3 | 70–72 | 320 / 320 |
| 24 | 3-CF$_3$ | H | CH$_2$CH$_2$F | 54.9 / 55.4 | 3.7 / 4.0 | 8.5 / 8.2 | 74–75 | 328 / 328 |
| 25 | 3-CF$_3$ | H | nC$_7$H$_{15}$ | 63.2 / 63.9 | 6.1 / 5.6 | 7.4 / 7.1 | 59–60 | 380 / 380 |
| 26 | 3-CF$_3$ | H | nC$_8$H$_{17}$ | 64.0 / 64.1 | 6.4 / 6.4 | 7.1 / 7.0 | 50–51 | 394 / 394 |
| 27 | 3-CF$_3$ | H | cyclobutyl | 60.7 / 60.5 | 4.5 / 4.5 | 8.3 / 8.2 | 46–48 | 336 / 336 |

TABLE 1-continued (I)

Structure: Ar-O-pyridine-C(O)-NR¹R² where Ar = Xₙ-substituted phenyl

| Example No. | Xₙ | R¹ | R² | C (Calc. Found) | H (Calc. Found) | N (Calc. Found) | Melting Point (°C.) | m/e (Theory Found) |
|---|---|---|---|---|---|---|---|---|
| 28 | 3-CF₃ | —CH₂—CH₂—N(CH₃)—CH₂—CH₂— | | 59.2 58.9 | 4.9 5.5 | 11.5 11.1 | oil | 365 365 |
| 29 | 3-CF₃ | CH₃ | CH₃ | 58.1 54.5 | 4.2 4.6 | 9.0 8.7 | oil | 310 310 |
| 30 | 3-CF₃ | H | OC₂H₅ | 55.2 55.9 | 4.0 4.0 | 8.6 8.4 | oil | 326 326 |
| 31 | 3-CF₃ | H | NHCO₂C₂H₅ | 52.0 51.9 | 3.8 4.0 | 11.4 11.3 | 100–101 | 369 369 |
| 32 | 3-CF₃ | H | CH₂CH₂OH | 55.2 55.0 | 4.0 4.9 | 8.6 8.6 | 48–49 | 326 326 |
| 33 | 3-CF₃ | H | O—CH₂CH=CH₂ | 56.8 56.3 | 3.8 4.0 | 8.3 8.2 | oil | 338 338 |
| 34 | 3-CF₃ | H | CH₂CF₃ | 49.4 49.9 | 2.7 2.9 | 7.7 7.6 | 89–90 | 364 364 |
| 35 | 3-CF₃ | H | CH₃ | 56.7 54.2 | 3.7 4.2 | 9.5 10.5 | 67–68 | 296 296 |
| 36 | 3-CF₃ | H | cyclopropyl | 59.6 60.2 | 4.0 4.1 | 8.7 8.7 | 53–54 | 322 322 |
| 37 | 3-CF₃ | H | CH₂CO₂C₂H₅ | 55.4 56.0 | 4.1 4.5 | 7.6 7.6 | 66–67 | 368 368 |
| 38 | 3-CF₃ | H | CON(CH₃)₂ | 54.4 57.1 | 4.0 4.7 | 11.9 11.9 | 136–137 | 353 353 |
| 39 | 3-CF₃ | CH₂CH=CH₂ | CH₂CH=CH₂ | 62.9 62.7 | 4.7 4.9 | 7.7 7.7 | 55–56 | 362 362 |
| 40 | 3-CF₃ | H | C(CH₃)₂—CN | 58.4 57.3 | 4.0 4.2 | 12.0 11.7 | 91–92 | 349 349 |
| 41 | 3-CF₃ | H | NH-phenyl | 61.1 58.5 | 3.7 3.6 | 11.3 10.3 | oil | 373 373 |
| 42 | 3-CF₃ | H | NH-(4-Cl-phenyl) | 56.0 55.7 | 3.2 3.2 | 10.3 9.9 | 100–101 | 407 |
| 43 | 3-CF₃ | H | NHCH₃ | 54.0 55.3 | 3.8 4.3 | 13.5 13.4 | oil | 311 311 |
| 44 | 3-CF₃ | H | CO₂C₂H₅ | 54.2 55.4 | 3.7 4.0 | 7.9 7.9 | 142–143 | 354 354 |
| 45 | 3-CF₃ | H | H | 55.3 56.2 | 3.2 3.6 | 9.9 9.7 | 134–135 | 282 282 |
| 46 | 3-C₂H₅ | H | CH₂CF₃ | 59.2 58.8 | 4.6 4.8 | 8.6 8.2 | oil | 324 324 |
| 47 | H | H | CH₂CF₃ | 56.7 56.9 | 3.7 4.1 | 9.5 9.1 | 104–105 | 296 296 |
| 48 | 3-CF₃ | H | cyclopentyl | 61.7 60.2 | 4.8 4.9 | 8.0 7.8 | oil | 350 350 |
| 49 | 3-CF₃ | H | cyclohexyl | 62.6 61.4 | 5.2 5.2 | 7.7 7.5 | oil | 364 364 |
| 50 | 3-OCH₃ | H | n-C₃H₇ | 67.1 66.6 | 6.3 6.5 | 9.8 9.8 | oil | 286 286 |
| 51 | 3-CF₃ | H | 2,2-Cl₂-cyclopropyl-methyl | 50.4 50.0 | 3.2 3.4 | 6.9 6.4 | oil | — |
| 52 | 3-CF₃ | CH₃ | 2,2-Cl₂-cyclopropyl-methyl | 51.6 51.3 | 3.6 3.8 | 6.7 6.3 | oil | — |
| 53 | 3-Cl | H | iC₃H₇ | 62.0 62.1 | 5.2 5.1 | 9.6 9.4 | oil | — |
| 54 | 3-Cl | H | nC₃H₇ | 62.0 | 5.2 | 9.6 | oil | — |

TABLE 1-continued

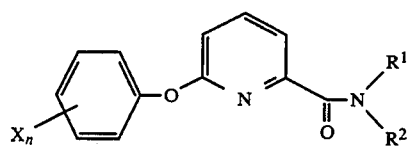

(I)

| Example No. | $X_n$ | $R^1$ | $R^2$ | C (Calc. Found) | H (Calc. Found) | N (Calc. Found) | Melting Point (°C.) | m/e (Theory Found) |
|---|---|---|---|---|---|---|---|---|
| 55 | 3-Cl | nC$_3$H$_7$ | nC$_3$H$_7$ | 61.6 65.0 64.6 | 5.0 6.4 6.2 | 9.9 8.4 8.1 | oil | — |
| 56 | 3-Cl | H | CH$_2$CF$_3$ | 50.9 51.3 | 3.1 2.9 | 8.5 8.9 | oil | — |
| 57 | 3-Cl | H | H | 58.0 58.0 | 3.7 3.8 | 11.3 11.7 | 186 | — |
| 58 | 3-Cl | H | CH$_2$CH$_2$F | 57.0 56.6 | 4.1 4.2 | 9.5 9.1 | oil | — |
| 59 | 3-Cl | CH$_3$ | 2,2-Cl$_2$-cyclopropyl-methyl | 52.9 52.4 | 3.9 3.6 | 7.3 6.9 | oil | — |
| 60 | 3-Cl | H | 2,2-Cl$_2$-cyclopropyl methyl | 51.7 51.5 | 3.5 3.2 | 7.5 7.0 | oil | — |
| 61 | 3-Cl | C$_2$H$_5$ | CH$_2$C≡CH$_2$ CH$_3$ | 65.4 65.4 | 5.8 6.1 | 8.5 8.5 | oil | — |

TABLE 2

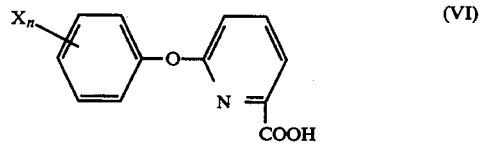

(VI)

| $X_n$ | C (Calc. Found) | H (Calc. Found) | N (Calc. Found) | Melting Point (°C.) | m/e (Theory Found) |
|---|---|---|---|---|---|
| 3-Cl | 57.8 57.4 | 3.2 3.2 | 5.6 5.5 | not recorded | 249 249 |
| 3,4-diCl | 50.9 52.3 | 2.5 3.7 | 4.9 5.4 | 110-111 | 283 283 |
| 3-CF$_3$,4-F | 51.8 51.9 | 2.3 3.0 | 4.7 4.3 | 86-87 | 301 301 |
| 3-Br | 49.0 53.0 | 2.7 3.2 | 4.8 4.8 | 76-77 | 294 294 |
| 3,5-diCl | 50.9 51.0 | 2.5 2.9 | 4.9 5.8 | 140-141 | 283 283 |
| 3-NO$_2$ | 55.4 54.4 | 3.1 2.6 | 10.8 10.8 | 147-149 | 260 260 |
| 3-C$_2$H$_5$ | 69.1 66.5 | 5.3 5.1 | 5.7 5.7 | 50-51 | 243 243 |
| H | 66.9 66.6 | 4.2 4.2 | 6.5 6.4 | 104-105 | 215 215 |
| 3-OCH$_3$ | 63.7 61.9 | 4.5 4.1 | 5.7 5.5 | 102-103 | 245 245 |

EXAMPLE 62

Preparation of N-n-propyl-2-(3-α,α,α,-trifluoromethylphenoxy)-6-pyridine carboxamide (a) 6-chloropicolinic acid (3 g) and thionyl chloride (50 ml) was refluxed for one hour. The excess thionyl chloride was evaporated in vacuo and dichloromethane added to the residual picolinoyl chloride. This solution was poured into an excess of n-propylamine in dichloromethane. The solution was then washed with water, dried over anhydrous magnesium sulphate and the dichloromethane evaporated to give 6-chloro-2-N-n-propyl pyridine carboxamide (3 g) as a yellow oil.

| Analysis (%): | | | | |
|---|---|---|---|---|
| C$_9$H$_{11}$N$_2$OCl: | Calc: | C 54.5 | H 5.5 | N 14.1 |
| | Found: | C 54.2 | H 5.9 | N 14.0 |
| m/e: | Theory: | 198 | | |
| | Found: | 198 | | |

(b) A solution of sodium methoxide (from 0.4 g of sodium in 20 ml of methanol) was added to a solution of 3-α,α,α-trifluoromethylphenol (2.6 g) in xylene (20 ml). The solvents were evaporated in vacuo to give the dry sodium phenolate. Pyridine (14 ml) and xylene (30 ml) were added, followed by cuprous chloride (0.4 g) and the mixture heated to reflux. A solution of 6-chloro-2-N-n-propyl pyridine carboxamide (3 g) in xylene (20 ml) was added dropwise and the resultant mixture refluxed a further 18 hours. After cooling, the mixture was poured into water and acidified with dilute hydrochloric acid. The whole was extracted with diethyl ether. The combined extracts were dried over anhydrous magnesium sulphate and evaporated. The residue was purified on a silica gel column using 5% (v/v) diethyl ether/dichloromethane as eluant to give recovered starting material (6-chloro-2-N-n-propyl pyridine carboxamide, 60%) and the title compound (40%) as a colourless oil.

EXAMPLE 63

Preparation of N-n-butyl-2-(3-α,α,α-trifluoromethylphenoxy)-6-pyridinethiocarboxamide A mixture of N-n-butyl-2-(3-α,α,α-trifluoromethylphenoxy)-6-pyridine carboxamide (0.6 g) and phosphorus pentasulphide (1.0 g) in pyridine (50 ml) was refluxed for 2 hours. The pyridine was evaporated and water added to the residue. The aqueous solution was then extracted with methylene chloride. The extracts were washed with dilute hydrochloric acid, water and dried over anhydrous magnesium sulphate. The dichloromethane was evaporated and the residue purified on a silica gel column using dichloromethane as eluant to give the title compound (0.5 g) as a yellow solid of melting point 61°–62° C.

| Analysis (%): | | | | |
|---|---|---|---|---|
| $C_{17}H_{17}N_2OSF_3$: | Calc: | C 57.6 | H 4.8 | N 7.9 |
| | Found: | C 61.0 | H 4.7 | N 8.1 |
| m/e: | Theory: | 354 | | |
| | Found | 354 | | |

EXAMPLE 64

Herbicidal Activity

To evaluate their herbicidal activity, compounds according to the invention were tested using as representative range of plants: maize, Zea mays (Mz); rice, Oryza sativa (R); barnyard grass, Echinochloa crusgalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death (i.e. 100% effectiveness). An increase of 1 unit on the linear scale approximates to a 10% increase in the level of effect.

The results of the tests are set out in the following Table 3 in which the compounds are identified by reference to the preceding examples. In the Table, a blank space indicates a 0 rating, and an asterisk indicates that do result was obtained.

TABLE 3

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 2 | 6 | 6 | 8 | 7 | 3 | 9 | 9 | 4 | 5 | 9 | 7 | 9 | 9 | 9 | 9 | 9 | 8 | 8 | 8 | 9 | 9 | 8 | 9 | 9 | 7 |
| | | | | | | | | | 1 | 6 | 5 | 9 | 7 | 8 | 9 | 9 | 8 | 6 | 6 | 9 | 8 | 6 | 9 | 9 | 7 |
| 3 | 3 | 3 | 7 | 6 | 5 | 9 | 7 | 3 | 5 | 8 | 8 | 9 | 8 | 8 | 9 | 9 | 8 | 7 | 6 | 9 | 9 | 7 | 9 | 9 | 5 |
| | | | | | | | | | 1 | 6 | 6 | 8 | 7 | 7 | 9 | 9 | 8 | 6 | 5 | 9 | 6 | 4 | 9 | 9 | 3 |
| 4 | 1 | 1 | 5 | 4 | 5 | 8 | 6 | 3 | 5 | 6 | 6 | 8 | 7 | 8 | 9 | 9 | 8 | 6 | 5 | 9 | 8 | 7 | 9 | 9 | 2 |
| | | | | | | | | | 1 | 5 | 4 | 8 | 7 | 7 | 9 | 9 | 8 | 5 | 4 | 9 | 7 | 6 | 9 | 9 | 1 |
| 5 | | | | | | | | | 5 | 7 | 2 | 8 | 7 | 6 | 9 | 9 | 8 | | | 6 | 4 | 1 | 9 | 8 | 3 |
| | | | | | | | | | 1 | 3 | | 6 | 4 | 5 | 9 | 9 | 7 | | | 1 | | | 7 | 6 | |
| 6 | 2 | | 5 | 3 | 3 | 7 | 6 | 1 | 5 | 7 | 6 | 8 | 6 | 8 | 9 | 9 | 7 | 2 | 4 | 9 | 2 | 3 | 9 | 8 | 2 |
| | | | | | | | | | 1 | 5 | 3 | 6 | 3 | 7 | 8 | 8 | 6 | 1 | 2 | 8 | | 1 | 8 | 8 | |
| 7 | 6 | 3 | 6 | 5 | 2 | 7 | 9 | 4 | 5 | 7 | 6 | 9 | 6 | 8 | 9 | 9 | 8 | 6 | 3 | 9 | 8 | 7 | 9 | 9 | 3 |
| | | | | | | | | | 1 | 5 | 2 | 7 | 4 | 7 | 9 | 9 | 7 | 2 | | 5 | 3 | 2 | 9 | 9 | |
| 8 | 5 | 5 | 6 | 4 | 5 | 7 | 7 | 2 | 5 | 5 | 4 | 9 | 7 | 8 | 9 | 9 | 8 | 5 | 4 | 9 | 6 | 7 | 9 | 9 | 5 |
| | | | | | | | | | 1 | 3 | 2 | 7 | 5 | 8 | 9 | 9 | 6 | 2 | 2 | 5 | | 3 | 8 | 8 | |
| 9 | 6 | 5 | 7 | 3 | 4 | 8 | 8 | 5 | 5 | 7 | 5 | 9 | 7 | 8 | 9 | 9 | 8 | 6 | 6 | 9 | 7 | 6 | 9 | 9 | 4 |
| | | | | | | | | | 1 | 6 | 5 | 9 | 6 | 8 | 9 | 9 | 7 | 2 | 5 | 8 | 4 | 3 | 8 | 9 | 2 |
| 10 | | | | | 3 | | | | 5 | 5 | 3 | 6 | 4 | 6 | 9 | 7 | 7 | | | | | | 4 | | |
| | | | | | | | | | 1 | 4 | | * | | 5 | 7 | * | 6 | | | | | | 2 | | |
| 11 | 4 | | 4 | | | 4 | 4 | 2 | 5 | 7 | 3 | 8 | 5 | 6 | 9 | 9 | 7 | | | | | | 6 | 4 | |
| | | | | | | | | | 1 | 6 | 2 | 7 | 4 | 5 | 8 | 9 | 6 | | | | | | 5 | | |
| 12 | 5 | | 5 | 1 | 4 | * | 9 | 1 | 5 | 8 | 5 | 9 | 6 | 8 | 9 | 9 | 8 | 6 | 4 | 9 | 7 | 7 | 9 | 9 | 5 |
| | | | | | | | | | 1 | 7 | 4 | 9 | 5 | 8 | 9 | 9 | 7 | 4 | 3 | 9 | 4 | 4 | 9 | 9 | 2 |
| 13 | | | | | | | | | 5 | 5 | 3 | 8 | 5 | 6 | 9 | 9 | 8 | 2 | 2 | 2 | | | 7 | 5 | |
| | | | | | | | | | 1 | 2 | | 7 | 2 | 5 | 8 | 9 | 6 | | | | | | 5 | 4 | |
| 14 | | | | | | | | | 5 | 5 | 3 | 7 | 5 | 5 | 7 | 8 | 5 | | | 4 | 1 | 1 | 7 | 7 | |
| | | | | | | | | | 1 | 3 | 1 | 3 | 2 | 3 | 6 | 6 | 3 | | | | | | 4 | | |
| 15 | 4 | | 3 | 2 | 1 | 2 | 2 | 1 | 5 | 5 | 4 | 8 | 7 | 7 | 9 | 9 | 7 | 4 | 2 | 9 | 5 | 4 | 9 | 9 | 2 |
| | | | | | | | | | 1 | 3 | 2 | 5 | 4 | 6 | 8 | 9 | 5 | 1 | | 6 | 2 | 2 | 8 | 7 | |
| 16 | 2 | | 4 | 2 | 3 | 3 | 4 | | 5 | 4 | 5 | 8 | 5 | 7 | 8 | 9 | 6 | 3 | 3 | 9 | 5 | 3 | 9 | 8 | |
| | | | | | | | | | 1 | 2 | 2 | 6 | 2 | 6 | 7 | 7 | 4 | 2 | | 7 | 2 | | 8 | 7 | |
| 17 | | | | | 1 | 1 | | | 5 | 6 | 3 | 4 | 2 | 6 | 8 | 9 | 6 | | | 2 | | | 2 | | |
| | | | | | | | | | 1 | 2 | 2 | 1 | 1 | 4 | 7 | 7 | 5 | | | | | | 1 | | |
| 18 | 3 | 3 | 5 | 1 | 3 | 5 | 6 | | 5 | 6 | 4 | 6 | 4 | 7 | 9 | 9 | 7 | 1 | | 4 | 2 | | 4 | 3 | 1 |
| | | | | | | | | | 1 | 4 | 2 | 3 | 2 | 6 | 8 | 9 | 7 | | | | | | 2 | 1 | |
| 19 | 4 | 3 | 5 | 4 | 5 | 6 | 6 | 3 | 5 | 7 | 6 | 9 | 6 | 8 | 9 | 9 | 8 | * | * | * | * | * | * | * | * |
| | | | | | | | | | 1 | 6 | 5 | 6 | 5 | 8 | 9 | 9 | 7 | * | * | * | * | * | * | * | * |
| 20 | | | 3 | 2 | 1 | 3 | 4 | | 5 | 7 | 6 | 8 | 7 | 8 | 9 | 9 | 7 | * | * | * | * | * | * | * | * |

TABLE 3-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 21 | | | | 2 | | 2 | 2 | | 1 | 5 | 4 | 6 | 4 | 7 | 9 | 9 | 6 | * | * | * | * | * | * | * | * |
| | | | | | | | | | 5 | 6 | 4 | 7 | 5 | 7 | 9 | 9 | 7 | 1 | * | 8 | 2 | 1 | 5 | 8 | 2 |
| 22 | 5 | 6 | 7 | 6 | 6 | 8 | 8 | 4 | 1 | 4 | 2 | 6 | 3 | 5 | 9 | 9 | 6 | | * | * | | | * | * | |
| | | | | | | | | | 5 | 7 | 6 | 8 | 7 | 8 | 9 | 9 | 8 | * | * | * | * | * | * | * | * |
| 23 | 3 | 2 | 5 | 3 | 4 | 6 | 7 | 3 | 1 | 5 | 4 | 7 | 4 | 8 | 9 | 9 | 7 | * | * | * | * | * | * | * | * |
| | | | | | | | | | 5 | 5 | 4 | 8 | 4 | 8 | 9 | 9 | 7 | 4 | 3 | 9 | 7 | 5 | 9 | 9 | 2 |
| 24 | * | * | * | * | * | * | * | * | 1 | 3 | 2 | 5 | 3 | 7 | 9 | 9 | 6 | 1 | | 7 | 5 | 3 | 8 | 8 | |
| | | | | | | | | | 5 | 8 | 7 | 9 | 7 | 8 | 9 | 9 | 7 | 6 | 5 | 9 | 8 | 9 | 9 | 9 | 9 |
| 25 | | | | | 2 | | | | 1 | 6 | 5 | 7 | 5 | 7 | 9 | 9 | 6 | 4 | 3 | 9 | 6 | 5 | 9 | 9 | 7 |
| | | | | | | | | | 5 | 3 | 2 | 5 | 3 | 4 | 9 | 9 | 6 | | | 5 | | 1 | 7 | 8 | |
| 26 | | | | | | | | | 1 | 3 | 1 | 3 | 1 | 2 | 9 | 9 | 4 | | | 3 | | | 3 | 7 | |
| | | | | | | | | | 5 | 5 | 2 | 4 | 3 | 5 | 9 | 9 | 6 | | 1 | 7 | 2 | 4 | 8 | 9 | 1 |
| 27 | 6 | 6 | 6 | 6 | 5 | 8 | 4 | 2 | 1 | 3 | 1 | 2 | 1 | 3 | 9 | 9 | 6 | | | 2 | | 2 | 6 | 9 | |
| | | | | | | | | | 5 | 8 | 7 | 8 | 8 | 8 | 9 | 9 | 8 | 7 | 7 | 9 | 9 | 9 | 9 | 9 | 8 |
| 28 | | | | | 2 | 2 | | | 1 | 6 | 5 | 7 | 6 | 8 | 9 | 9 | 7 | 6 | 5 | 9 | 8 | 8 | 9 | 9 | 8 |
| | | | | | | | | | 5 | 4 | 4 | 6 | 3 | 5 | 9 | 9 | 7 | | | 2 | | 1 | 7 | 8 | |
| 29 | 5 | | 4 | 2 | 5 | 7 | 7 | 5 | 1 | 3 | 2 | 5 | 2 | 4 | 8 | 8 | 5 | | | 1 | | | 5 | 7 | |
| | | | | | | | | | 5 | 4 | 3 | 7 | 4 | 7 | 9 | 9 | 7 | 7 | 3 | 9 | 6 | 3 | 9 | 9 | 2 |
| 30 | 5 | 2 | 2 | | | 4 | 7 | 5 | 2 | 1 | 3 | 1 | 4 | 2 | 5 | 9 | 9 | 6 | 3 | 1 | 6 | | 1 | 8 | 9 | |
| | | | | | | | | | 5 | 7 | 5 | 7 | 3 | 6 | 9 | 9 | 7 | 7 | 2 | 9 | | 8 | 9 | 9 | 1 |
| 31 | 4 | | 2 | | | 4 | | | 1 | 5 | 3 | 5 | 2 | 4 | 9 | 9 | 5 | 4 | | 7 | | 7 | 9 | 9 | |
| | | | | | | | | | 5 | 2 | 1 | 9 | 5 | 5 | 9 | 9 | 6 | 4 | | 7 | | 1 | 7 | 5 | 3 |
| 32 | 6 | 3 | 6 | 2 | | 7 | 4 | | 1 | | | 4 | 2 | 3 | 8 | 8 | 4 | | | 4 | | | 4 | 3 | 1 |
| | | | | | | | | | 5 | 5 | 3 | 9 | 5 | 6 | 9 | 9 | 7 | 5 | | 7 | 3 | | 8 | 8 | 5 |
| 33 | 7 | * | * | * | 3 | 7 | 3 | 3 | 1 | 3 | | 7 | 4 | 3 | 9 | 9 | 5 | 2 | | 4 | | | 6 | 5 | 4 |
| | | | | | | | | | 5 | 7 | 4 | 9 | 6 | 8 | 9 | 9 | 8 | 6 | | 8 | 3 | 6 | 9 | 9 | 2 |
| 34 | 6 | 6 | 8 | 7 | 6 | 8 | 7 | 2 | 1 | 5 | 3 | 7 | 4 | 7 | 9 | 9 | 7 | 4 | | 7 | | 4 | 9 | 8 | 1 |
| | | | | | | | | | 5 | 8 | 8 | 8 | 8 | 8 | 9 | 9 | 8 | 8 | 7 | 9 | 9 | 9 | 9 | 9 | 8 |
| 35 | 6 | 6 | 8 | 5 | 5 | 6 | 9 | 5 | 1 | 8 | 8 | 8 | 8 | 8 | 9 | 9 | 9 | 7 | 6 | 9 | 9 | 7 | 9 | 9 | 7 |
| | | | | | | | | | 5 | 8 | 6 | 9 | 9 | 8 | 9 | 9 | 8 | 7 | 7 | 9 | 8 | 8 | 9 | 9 | 6 |
| 36 | * | * | * | * | * | * | * | * | 1 | 5 | 3 | 8 | 5 | 7 | 8 | 9 | 7 | 5 | 4 | 9 | 6 | 6 | 9 | 9 | 3 |
| | | | | | | | | | 5 | 9 | 8 | 9 | 9 | 8 | 9 | 9 | 8 | 7 | 6 | 9 | 8 | 8 | 9 | 9 | 7 |
| 37 | | | | | | | | | 1 | 7 | 6 | 8 | 6 | 8 | 9 | 9 | 8 | * | 4 | 9 | 7 | 6 | 8 | 9 | 6 |
| | | | | | | | | | 5 | 7 | 4 | 9 | 6 | 6 | 9 | 9 | 7 | | | | | | | 5 | 3 |
| 38 | 2 | | 4 | 1 | 2 | 4 | 1 | | 1 | 3 | 2 | 6 | 2 | 5 | 8 | 8 | 5 | | | | | | | 3 | |
| | | | | | | | | | 5 | 6 | 1 | 7 | 3 | 7 | 7 | 8 | 7 | 4 | 1 | 7 | 1 | 4 | 7 | 8 | 4 |
| 39 | 1 | | 1 | 1 | 5 | 6 | 3 | | 1 | 4 | 1 | 5 | 1 | 5 | 7 | 7 | 6 | 1 | | 2 | | 1 | 5 | 4 | |
| | | | | | | | | | 5 | 8 | 3 | 7 | 5 | 7 | 9 | 8 | 7 | 4 | | 8 | 3 | 5 | 8 | 8 | 7 |
| 40 | 4 | 3 | 6 | 5 | 4 | 7 | 4 | 2 | 1 | 5 | | 6 | 2 | 6 | 8 | 7 | 6 | 1 | | 6 | | 1 | 7 | 5 | 3 |
| | | | | | | | | | 5 | 7 | 4 | 7 | 5 | 7 | 8 | 8 | 7 | 4 | 1 | 8 | 4 | 5 | 8 | 9 | 4 |
| 41 | | | | | | | | | 1 | 4 | | 6 | 2 | 6 | 8 | 8 | 6 | 1 | | 7 | 3 | 3 | 7 | 8 | |
| | | | | | | | | | 5 | 4 | | 4 | | 5 | 9 | 7 | 5 | | | | | | 4 | 2 | |
| 42 | | | | | | | | | 1 | 2 | | 2 | | 2 | 8 | 6 | 5 | | | 1 | | | | | |
| | | | | | | | | | 5 | 5 | | 4 | | 4 | 8 | 6 | 4 | | | | | | | | |
| 43 | | | | | | | | | 1 | | | 1 | | 1 | 6 | 2 | 1 | | | | | | | | |
| | | | | | | | | | 5 | 5 | | 8 | 3 | 2 | 6 | 7 | 4 | | | | | | | | |
| 44 | 2 | | | | | 3 | 2 | 1 | 1 | 3 | | 2 | | 3 | 3 | 1 | | | | | | | | | |
| | | | | | | | | | 5 | 2 | 1 | 6 | 2 | 4 | 9 | 8 | 7 | | | | | | 2 | | |
| 45 | | | 1 | | | 1 | | | 1 | 1 | | 5 | 1 | 3 | 8 | 7 | 6 | | | | | | 1 | | |
| | | | | | | | | | 5 | | | 3 | 2 | 4 | 8 | 8 | 6 | | | 2 | | | 5 | 4 | |
| 46 | | | 5 | 3 | 2 | 3 | 5 | 2 | 1 | | | 1 | 1 | 2 | 8 | 7 | 5 | | | | | | 2 | 1 | |
| | | | | | | | | | 5 | 4 | 4 | 8 | 5 | 7 | 9 | 9 | 8 | | | 8 | 2 | 4 | 8 | 9 | 5 |
| 47 | | | 4 | | | 4 | | 1 | 1 | 1 | 2 | 7 | 4 | 6 | 8 | 8 | 7 | | | 4 | 1 | | 4 | 4 | |
| | | | | | | | | | 5 | 3 | 1 | 7 | 4 | 6 | 9 | 9 | 7 | 1 | | 5 | | 3 | 8 | 7 | 2 |
| 48 | 5 | 2 | 8 | 6 | 4 | 6 | 8 | 5 | 1 | 1 | | 4 | 2 | 3 | 8 | 7 | 6 | | | 2 | | | 1 | 2 | |
| | | | | | | | | | 5 | 6 | 7 | 9 | 8 | 8 | 9 | 9 | 7 | 5 | 5 | 9 | 7 | 6 | 9 | 9 | 8 |
| 49 | 2 | | 8 | 6 | 4 | 7 | 7 | 3 | 1 | * | * | * | * | * | * | * | * | * | * | * | * | * | * | * | * |
| | | | | | | | | | 5 | 6 | 7 | 9 | 7 | 8 | 9 | 9 | 7 | 5 | 4 | 9 | 6 | 6 | 9 | 9 | 5 |
| 50 | 1 | | 5 | | 1 | 3 | 7 | 3 | 1 | 5 | 4 | 9 | 6 | 7 | 9 | 9 | 7 | 2 | 1 | 8 | 5 | 4 | 8 | 8 | 2 |
| | | | | | | | | | 5 | 3 | | 9 | 3 | 6 | 8 | 9 | 6 | | | 3 | | | 2 | 2 | 2 |
| 51 | 3 | | | 4 | 3 | 4 | 4 | 3 | 1 | 2 | | 8 | 1 | 4 | 7 | 8 | 6 | | | | | | | 1 | |
| | | | | | | | | | 5 | 6 | 5 | 8 | 6 | 7 | 9 | 9 | 9 | 6 | | 8 | 6 | 4 | 8 | 9 | 6 |
| 52 | | | | | 3 | 4 | 7 | | 1 | 5 | 2 | 7 | 5 | 6 | 9 | 9 | 8 | 2 | | 7 | 4 | 2 | 8 | 9 | 5 |
| | | | | | | | | | 5 | 7 | 3 | 9 | 5 | 7 | 9 | 9 | 7 | 1 | | 3 | 2 | 2 | 7 | 4 | |
| 53 | 3 | | 5 | 2 | 1 | 3 | 5 | | 1 | 4 | 2 | 4 | 4 | 7 | 9 | 9 | 6 | | | 1 | 1 | | 4 | 2 | |
| | | | | | | | | | 5 | 5 | 5 | 9 | 6 | 7 | 9 | 9 | 8 | 5 | | 9 | 5 | 5 | 8 | 8 | |
| 54 | 6 | 3 | 7 | 4 | 3 | 6 | 5 | | 1 | 4 | 2 | 8 | 5 | 6 | 8 | 9 | 7 | | | 5 | | | 7 | 7 | |
| | | | | | | | | | 5 | 7 | 6 | 9 | 6 | 7 | 9 | 9 | 8 | 6 | 5 | 9 | 7 | 6 | 9 | 9 | 1 |
| 55 | 3 | | 4 | | 2 | 3 | 2 | | 1 | 5 | 2 | 8 | 2 | 5 | 9 | 9 | 7 | 3 | | 9 | 2 | 2 | 7 | 8 | |
| | | | | | | | | | 5 | 5 | 3 | 9 | 6 | 6 | 9 | 9 | 7 | 4 | | 9 | 2 | 3 | 8 | 8 | |
| 56 | 6 | 4 | 5 | 4 | 3 | 6 | 5 | 4 | 1 | 4 | | 8 | 4 | 5 | 9 | 9 | 7 | 1 | | 3 | | | 7 | 5 | |
| | | | | | | | | | 5 | 7 | 4 | 9 | 6 | 7 | 9 | 9 | 7 | 6 | 4 | 9 | 7 | 7 | 9 | 9 | 4 |
| 57 | | | | | | 3 | 2 | | 1 | 5 | 1 | 9 | 3 | 7 | 9 | 9 | 7 | 5 | | 9 | 6 | 6 | 8 | 9 | |
| | | | | | | | | | 5 | 5 | 2 | 3 | 2 | 5 | 9 | 8 | 7 | 1 | | 2 | | | 7 | 5 | 1 |
| 58 | 6 | 4 | 5 | 4 | 4 | 6 | 7 | 4 | 1 | 3 | | 2 | | 4 | 8 | 8 | 5 | | | | | | 2 | | |
| | | | | | | | | | 5 | 7 | 5 | 8 | 5 | 8 | 9 | 9 | 7 | 4 | 3 | 8 | 5 | 4 | 9 | 9 | 2 |
| 59 | | | | | | | | | 1 | 4 | 3 | 6 | 3 | 6 | 9 | 8 | 6 | 2 | | 5 | 2 | 1 | 7 | 8 | |
| | | | | | | | | | 5 | 5 | 2 | 5 | 2 | 6 | 9 | 8 | 6 | | | | | | | | |
| | | | | | | | | | 1 | 2 | | 2 | 1 | 4 | 8 | 8 | 5 | | | | | | | | |

TABLE 3-continued

| Compound of Ex. No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 60 | | | | | | | 3 | | 5 | 6 | 5 | 6 | 2 | 5 | 9 | 9 | 6 | | | 2 | 1 | | 3 | 2 | |
| | | | | | | | | | 1 | 3 | 2 | 3 | | 5 | 8 | 9 | 6 | | | | | | 1 | 2 | |
| 61 | | | | | | | | | 5 | 5 | 2 | 7 | 2 | 6 | 9 | 9 | 4 | | | | | | | | |
| | | | | | | | | | 1 | 3 | | | 3 | | 3 | 7 | 3 | | | | | | | | |
| 63 | 4 | 2 | 4 | 4 | 2 | 4 | 3 | | 5 | 5 | 6 | 8 | 6 | 6 | 8 | 9 | 8 | 2 | | 8 | 6 | 4 | 8 | 9 | 4 |
| | | | | | | | | | 1 | 3 | 3 | 8 | 4 | 4 | 8 | 9 | 8 | | | 5 | 4 | 2 | 7 | 4 | |

We claim:

1. A compound of the formula I

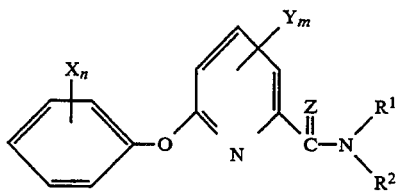

wherein n is an integer from 1 to 5 and each X independently represents a hydrogen or halogen atom, an alkyl or alkoxy group optionally substituted by one or more of the same or different substituents selected from halogen atoms and cyano, hydroxy and alkoxy groups, or a cyano, nitro, alkenyloxy, alkynyloxy, alkylthio, haloalkylthio, alkenylthio or alkynylthio group;

m is 0 or an integer from 1 to 3 and each Y independently represents a halogen atom or an alkyl or haloalkyl group;

Z represents an oxygen atom or a sulphur atom; and $R^1$ and $R^2$ each, independently, represents a hydrogen atom, an alkyl group optionally substituted by one or more of the same or different substituents selected from halogen atoms or hydroxy, cyano, alkoxy, alkylthio, alkoxycarbonyl, or mono- or di-alkylamino groups, an alkenyl, alkynyl, or a hydroxy, alkoxy, alkenyloxy, alkynyloxy, alkoxycarbonyl, amino, mono- or di-alkylamino, alkoxycarbonylamino group, an arylamino group optionally substituted by a halogen atom, or a dialkylcarbamoyl group; or $R^1$ and $R^2$ together represent an alkylene chain which is optionally interrupted by an oxygen or sulphur atom or by a group —NR— in which R represents a hydrogen atom or an alkyl group.

2. A herbicidal composition which comprises an effective amount of a compound defined by formula I

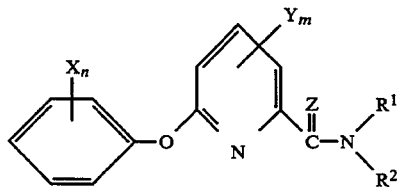

wherein n is an integer from 1 to 5 and each X independently represents a hydrogen or halogen atom, an alkyl or alkoxy group optionally substituted by one or more of the same or different substituents selected from halogen atoms and cyano, hydroxy and alkoxy groups, or a cyano, nitro, alkenyloxy, alkynyloxy, alkylthio, haloalkylthio, alkenylthio or alkynylthio group;

m is 0 or an integer from 1 to 3 and each Y independently represents a halogen atom or an alkyl or haloalkyl group;

Z represents an oxygen atom or a sulphur atom;

$R^1$ and $R^2$ each, independently, represents a hydrogen atom, an alkyl group optionally substituted by one or more of the same or different substituents selected from halogen atoms or hydroxy, cyano, alkoxy, alkylthio, alkoxycarbonyl, or mono- or di-alkylamino groups, an alkenyl, alkynyl, or a hydroxy, alkoxy, alkenyloxy, alkynyloxy, alkoxycarbonyl, amino, mono- or di-alkylamino, alkoxycarbonylamino group, an arylamino group optionally substituted by a halogen atom, or a dialkylcarbamoyl group; or $R^1$ and $R^2$ together represent an alkylene chain which is optionally interrupted by an oxygen or sulphur atom or by a group —NR— in which R represents a hydrogen atom or an alkyl group together with a carrier.

3. A composition as claimed in claim 2, wherein n is 1 or 2 and each X independently represents a hydrogen, fluorine, chlorine or bromine atom or a nitro, ethyl, methoxy or trifluoromethyl group.

4. A composition as claimed in claim 3, wherein n is 1 and X represents a 3-trifluoromethyl or 3-methoxy group or a 3-chlorine atom.

5. A composition as claimed in claim 4, wherein either $R^1$ represents a hydrogen atom or a $C_{1-4}$ alkyl or $C_{2-4}$ alkenyl group, while $R^2$ represents a hydrogen atom or an unsubstituted $C_{1-8}$ alkyl group, a $C_{1-4}$ alkyl group substituted by fluorine, hydroxy, cyano, $C_{1-2}$ alkoxy, ($C_{1-2}$ alkoxy)carbonyl or mono- or di-($C_{1-2}$ alkyl)amino, a $C_{2-4}$ alkenyl group, a $C_{2-4}$ alkynyl group, a $C_{1-4}$ alkoxy group, a ($C_{1-4}$ alkyl)amino group, a $C_{2-4}$ alkenyloxy group, a ($C_{1-2}$ alkoxy)carbonyl group, a ($C_{1-2}$ alkoxy)carbonylamino group, a di($C_{1-2}$ alkyl)carbamoyl group, or an arylamino group in which the aryl group is optionally halo-substituted; or $R^1$ and $R^2$ together represent a group —$(CH_2)_4$—, —$(CH_2)_2O(CH_2)_2$— or —$(CH_2)_2NR(CH_2)_2$— in which R is a $C_{1-2}$ alkyl group.

6. A composition as claimed in claim 5, wherein either $R^1$ represents a hydrogen atom while $R_2$ represents an unsubstituted $C_{1-5}$ alkyl group, a $C_{1-2}$ alkyl group substituted by fluorine or methoxy, a $C_3$ alkenyl group, a $C_3$ alkynyl group, a $C_{1-2}$ alkoxy group, or a $C_3$ alkenyloxy group, or $R^1$ represents a $C_{1-3}$ alkyl group while $R^2$ represents the same $C_{1-3}$ alkyl group.

7. A composition as claimed in claim 6, wherein $R^1$ represents a hydrogen atom and $R^2$ represents an ethyl or propyl group.

8. A method of combating undesired plant growth at a locus, which method comprises treating the locus with an effective amount of a compound defined by formula I

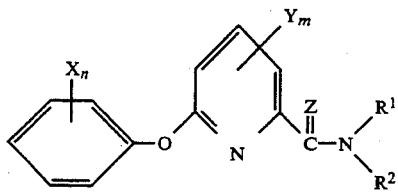

wherein n is an integer from 1 to 5 and each X independently represents a hydrogen or halogen atom, an alkyl or alkoxy group optionally substituted by one or more of the same or different substituents selected from halogen atoms and cyano, hydroxy and alkoxy groups, or a cyano, nitro, alkenyloxy, alkynyloxy, alkylthio, haloalkylthio, alkenylthio or alkynylthio group;

m is 0 or an integer from 1 to 3 and each Y independently represents a halogen atom or an alkyl or haloalkyl group;

Z represents an oxygen atom or a sulphur atom;

$R^1$ and $R^2$ each, independently, represents a hydrogen atom, an alkyl group optionally substituted by one or more of the same or different substituents selected from halogen atoms or hydroxy, cyano, alkoxy, alkylthio, alkoxycarbonyl, or mono- or di-alkylamino groups, an alkenyl, alkynyl, cycloalkyl, or optionally substituted cycloalkylalkyl group, or a hydroxy, alkoxy, alkenyloxy, alkynyloxy, alkoxycarbonyl, amino, mono- or di-alkylamino, alkoxycarbonylamino group, an arylamino group optionally substituted by a halogen atom, or a dialkylcarbamoyl group; or $R^1$ and $R^2$ together represent an alkylene chain which is optionally interrupted by an oxygen or sulphur atom or by a group —NR— in which R represents a hydrogen atom or an alkyl group together with a carrier.

9. A method of combating undesired plant growth at a locus, which method comprises treating the locus with an effective amount of a composition as claimed in claim 2.

* * * * *